(12) United States Patent
Suzuki (10) Patent No.: US 7,344,249 B2
(45) Date of Patent: Mar. 18, 2008

(54) OPHTHALMIC APPARATUS

(75) Inventor: Naoto Suzuki, Aichi (JP)

(73) Assignee: Nidek Co., Ltd., Aichi (JP)

( * ) Notice: Subject to any disclaimer, the term of this patent is extended or adjusted under 35 U.S.C. 154(b) by 457 days.

(21) Appl. No.: 10/953,443

(22) Filed: Sep. 30, 2004

(65) Prior Publication Data

US 2005/0122476 A1 Jun. 9, 2005

(30) Foreign Application Priority Data

Sep. 30, 2003 (JP) .................. P. 2003-340140

(51) Int. Cl.
*A61B 3/02* (2006.01)
(52) U.S. Cl. .................. 351/237; 351/239; 351/211; 351/221
(58) Field of Classification Search .................. 351/237
See application file for complete search history.

(56) References Cited

U.S. PATENT DOCUMENTS 5,550,602 A * 8/1996 Braeuning .................. 351/243
6,092,058 A * 7/2000 Smyth .......................... 706/10
6,705,726 B2 3/2004 Tanassi et al.
2005/0122477 A1* 6/2005 Alster et al. ................. 351/237
2005/0213033 A1* 9/2005 Sabel .......................... 351/203

FOREIGN PATENT DOCUMENTS

JP 7-67833 A 3/1995
WO WO 93/18702 A1 9/1993

\* cited by examiner

*Primary Examiner*—Jessica T Stultz
(74) *Attorney, Agent, or Firm*—Sughrue Mion, PLLC (57) ABSTRACT

An ophthalmic apparatus for examining and evaluating a visual function of an eye of a patient, includes: a presentation unit which presents an examination target to the patient's eye; a storage unit which stores therein subjective information obtained from the patient as to whether or not the patient can visually recognize the presented examination target; a calculation unit which calculates an objective evaluation value for the patient's eye using a fuzzy theory expressed as a probability function, based upon the stored subjective information; and an output unit which outputs the calculated evaluation value.

5 Claims, 5 Drawing Sheets

|  |  |  |  |  | | | | | |
|---|---|---|---|---|---|---|---|---|---|
|  |  |  |  | <0 | <0 | 4 | 18 |  |  |
|  |  |  | <0 | <0 | <0 | 0 | 4 | 20 |  |
|  |  | <0 | <0 | <0 | <0 | 12 | 0 | 12 | 24 |
|  | <0 | <0 | <0 | <0 | <0 | 16 | 20 | 14 | 24 | 26 |
|  | <0 | <0 | <0 | <0 | <0 | 4 | 8 |  | 26 | 30 |
| 26 | 28 | 28 | 32 | 32 | 32 | 28 |  | 24 | 28 |
| 26 | 26 | 28 | 32 | 32 | 32 | 32 | 24 | 24 | 26 |
|  | 24 | 26 | 28 | 28 | 28 | 28 | 28 | 28 |  |
|  |  | 24 | 24 | 24 | 24 | 28 | 24 |  |  |
|  |  |  | 20 | 24 | 26 | 26 |  |  |  |

FIG. 5B

|  |  |  |  |  | | | | | |
|---|---|---|---|---|---|---|---|---|---|
|  |  |  | <0.5 | <0.5 | <0.5 | - |  |  |  |
|  |  | <0.5 | <0.5 | <0.5 | <0.5 | <1 | - |  |  |
|  | <0.5 | <0.5 | <0.5 | <0.5 | <0.5 | <0.5 | <2 | - |  |
| <0.5 | <0.5 | <0.5 | <0.5 | <0.5 | <1 | <2 | <1 | - | - |
| <0.5 | <0.5 | <0.5 | <0.5 | <0.5 | <0.5 | <0.5 |  |  |  |
| - | - | - | - | - | - | - | <5 | - |  |
| - | - | - | - | - | - | - | <5 | - | - |
|  |  | - | - | - | - | - | - |  |  |
|  |  |  | - | - | - | - |  |  |  |
|  |  |  |  | - | - | - |  |  |  |

OPHTHALMIC APPARATUS

BACKGROUND OF THE INVENTION

The present invention relates to an ophthalmic apparatus for examining and evaluating a visual function of a patient's eye.

WO93/18702 discloses a perimeter for examining (measuring) the field of view of a patient's eye. The perimeter presents examination targets (stimulation targets) at various positions on an inside of a semi-spherical perimetry dome around an eye fixation point (eye fixation target) to which the patient's eye is visually fixed, and obtains information as to whether or not the patient can visually recognize these examination targets. On the basis of the obtained information, the perimetry for the patient's eye is conducted. An ophthalmic apparatus, such as the disclosed perimeter, for examining a visual function of a patient's eye merely outputs (displays and/or prints) the obtained results, on the basis of which a doctor must judge and evaluate whether or not the patient has an eye disease such as a perimetric disease. However, the evaluation based on the obtained results requires skill and experience, and therefore the result of the evaluation may differ depending on individual doctors.

SUMMARY OF THE INVENTION

A technical object of the present invention is to provide an ophthalmic apparatus capable of objectively examining and evaluating a visual function of a patient's eye.

To solve the above-described problems, an ophthalmic apparatus, according to the present invention, is featured by the following arrangements, (1) An ophthalmic apparatus for examining and evaluating a visual function of an eye of a patient, comprising:
   a presentation unit which presents an examination target to the patient's eye;
   a storage unit which stores therein subjective information obtained from the patient as to whether or not the patient can visually recognize the presented examination target;
   a calculation unit which calculates an objective evaluation value for the patient's eye using a fuzzy theory expressed as a probability function, based upon the stored subjective information; and
   an output unit which outputs the calculated evaluation value.

(2) An ophthalmic apparatus of (1), wherein:
   the calculation unit employs a membership function based on a curve of probability-of-seeing as the probability function.

(3) An ophthalmic apparatus of (1), wherein:
   the calculation unit calculates a value indicative of prevalence of the patient's eye as the evaluation value.

(4) An ophthalmic apparatus of (1), wherein:
   the ophthalmic apparatus includes:
   a perimeter for examining and evaluating a perimetric condition of the patient's eye.

(5) An ophthalmic apparatus of (4), wherein:
   the presentation unit presents, as the examination target, a perimetric stimulation target at each of various positions around a predetermined eye fixation point.

(6) An ophthalmic apparatus for examining and evaluating a perimetric condition of an eye of a patient, comprising:
   a presentation unit which presents an examination target at each of various positions around an eye fixation point to which the patient eye is visually fixed;
   a storage unit which stores therein luminance information of the examination target when the patient can visually recognize the presented examination target;
   a calculation unit which calculates an objective evaluation value for the patient's eye using a fuzzy theory expressed as a probability function, based on the stored luminance information; and
   an output unit which outputs the calculated evaluation value.

(7) An ophthalmic apparatus of (6) wherein:
   the storage unit stores therein a threshold value of a visual sensitivity corresponding to the luminance of the presented examination target as the luminance information when the patient can visually recognize the presented examination target.

(8) An ophthalmic apparatus of (6) wherein:
   the calculation unit employs a membership function based on a curve of probability-of-seeing as the probability function.

(9) An ophthalmic apparatus of (6) wherein:
   the calculation unit calculates a value indicative of prevalence of the patient's eye as the evaluation value.

DETAILED DESCRIPTION OF PREFERRED EMBODIMENTS

Figure 1:
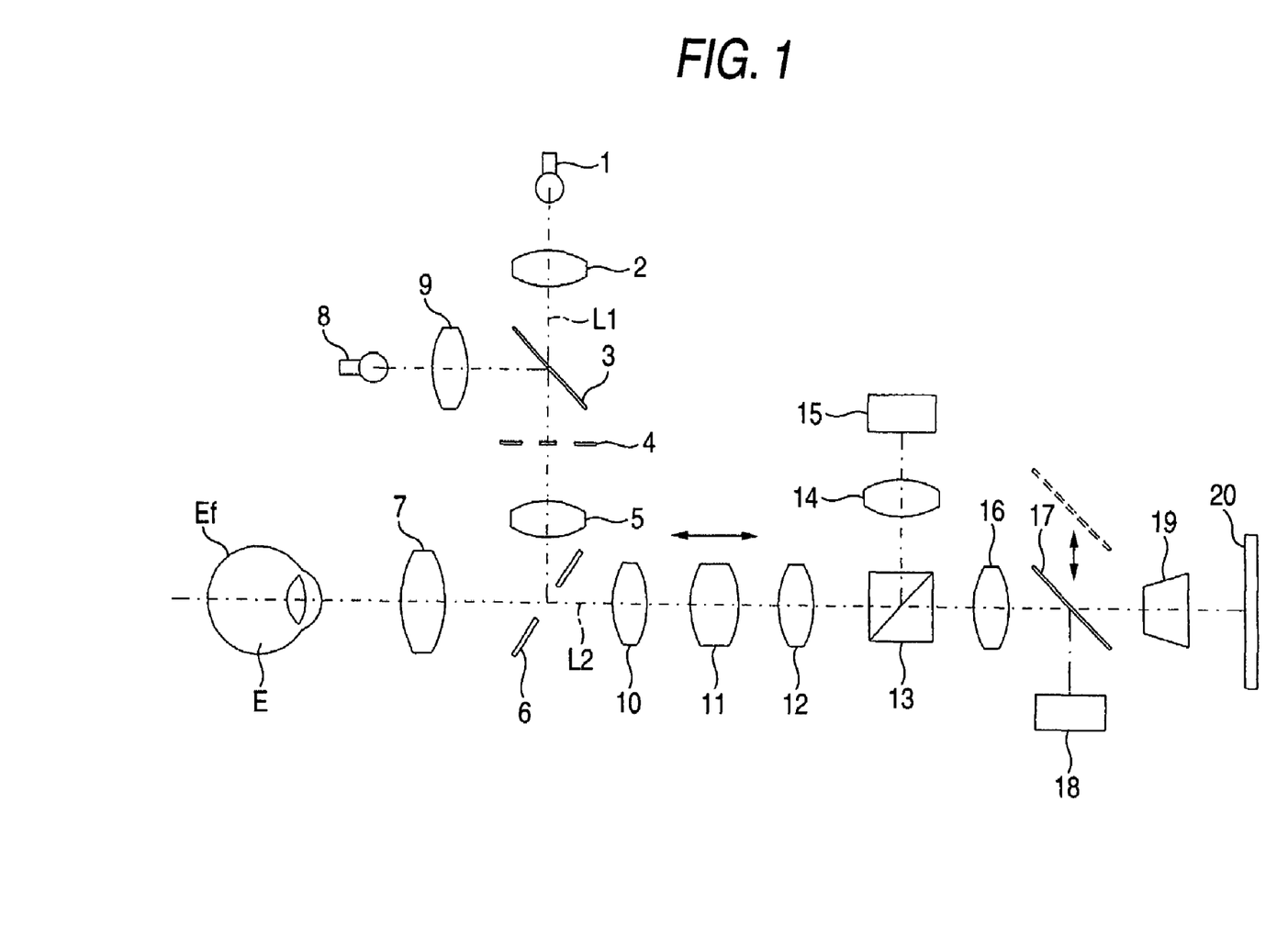
FIG. 1 is a schematic structural diagram as to an optical system of an ophthalmic apparatus according to an embodiment of the present invention.
Figure 2:
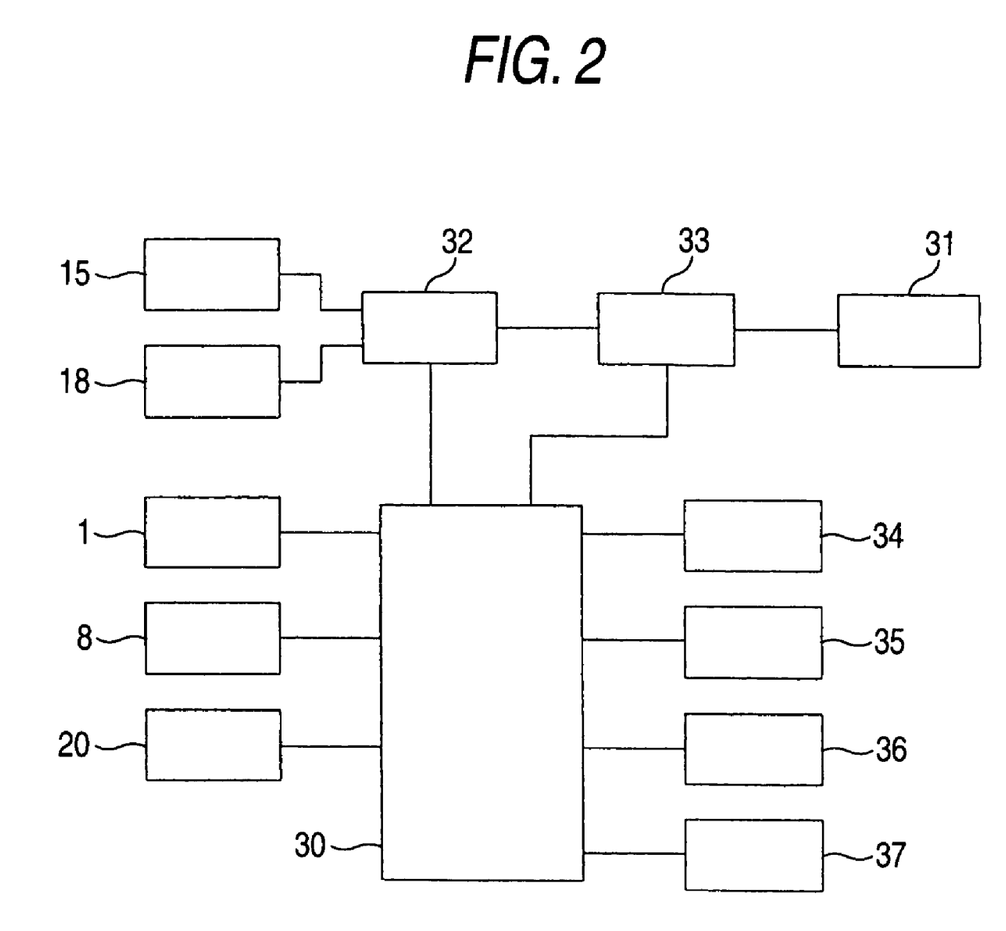
FIG. 2 is a schematic block diagram for showing a control system of the ophthalmic apparatus.

Referring now to drawings, an embodiment of the present invention will be described. FIG. 1 is a schematic structural diagram showing an optical system of an ophthalmic apparatus according to this embodiment, which has a fundus camera function and a perimeter function. FIG. 2 is a schematic block diagram of a control system of this ophthalmic apparatus.

In FIG. 1, symbol "E" shows a patient's eye, i.e. an eye to be examined. Light emitted from an observation-purpose illumination light source 1 such as a halogen lamp is converted into infrared illumination light by an infrared transmission filter (not shown) that illuminates a slit plate 4 having a ring slit 4a via a condenser lens 2 and a dichroic mirror (cold mirror) 3. The light (ring slit light) which has passed through the ring slit 4a forms an intermediate image in the vicinity of an aperture (opening) of a hole mirror 6 via a relay lens 5, and also, is reflected by a peripheral plane of the mirror 6 around the aperture. The light reflected by the mirror 6 is once focused in the vicinity of a pupil of the eye E by an objective lens 7, and thereafter, is diffused so as to illuminate a fundus "Ef" of the eye E uniformly. The mirror 3 has such a wavelength selection characteristic as to reflect visible light thereby, while passing infrared light therethrough. On the other hand, visible illumination light emitted from a photographing-purpose (imaging-purpose) illumination light source 8 such as a xenon flash lamp is traveled via another condenser lens 9 and the mirror 3, and is transmitted via the optical elements from the slit plate 4 to the lens 7 to illuminate the fundus Ef of the eye E similarly to the infrared illumination light. An illumination optical system (namely, both observation-purpose illumination optical system and photographing-purpose optical system) is formed by this construction. In addition, instead of the light source 1 and the infrared transmission filter, an infrared illumination light source may be alternatively employed.

The infrared reflection light reflected from the fundus Ef of the eye E is traveled through the lens 7, the mirror 6, lenses 10, 11, 12, a dichroic mirror 13, and a lens 14 to be focused onto a light receiving plane of an observation-purpose camera 15 having a sensitivity in an infrared region. The mirror 13 has such a wavelength selection characteristic as to reflect infrared light thereby, while passing visible light therethrough. The lens 11 is movable in an optical axis direction to put the fundus Ef of the eye E and the light receiving plane of the camera 15 into a conjugate positional relationship. An observation optical system is constructed in this fashion.

On the other hand, visible reflection light reflected from the fundus Ef of the eye E is traveled via optical elements from the lens 7 to the mirror 13 similarly to the infrared reflection light, and is transmitted via a lens 16 and a reflection mirror 17 to be focused onto a light receiving plane of a photographing-purpose (imaging-purpose) camera 18 having a sensitivity in a visible region. The light receiving plane of the camera 18 and the light receiving plane of the camera 15 are positioned to have a conjugate positional relationship. A photographing (imaging) optical system is formed in this manner.

The optical axis L1 of the illumination optical system (lenses 2, 5, 9) and an optical axis L2 of the observation optical system and photographing optical system (lenses 10, 12, 14, 16) are coaxial with respect to an optical axis of the lens 7.

The optical system used in the perimetry is arranged by commonly using the optical elements from the lens 7 to the lens 16 of the photographing optical system, and by employing a reducing lens 19 and a liquid crystal display (LCD) 20 for presenting an examination target (stimulation target). The lens 19 is employed so as to focus an entire image of the target presenting region of the LCD 20 onto the light receiving plane of the camera 15 in combination with an image of the fundus Ef of the eye E. When the perimetry is carried out (when the examination target is presented), the mirror 17 is moved out of the optical path. The examination target presented on the LCD 20 is projected via the optical elements from the lens 19 to the objective lens 7 onto the fundus Ef of the eye E. An eye fixation target (eye fixation point) having a cross shape is formed on a center (on the optical axis "L2") of the LCD 20. As to the examination target, a presenting position thereof, luminance thereof, a dimension thereof, and others can be varied.

The light source 1, the light source 8, the LCD 20, an image processing unit 32, an image switching unit 33, a memory 34, a response button 35, an input device 33 such as a mouse, an operation unit 37 equipped with various sorts of switches and keys, and the like are connected to a control unit 30. This control unit 30 is employed so as to drive/control an entire system of the ophthalmic apparatus. The button 35 is pushed (manipulated) when a patient, i.e. an person under examination, can visually recognize a presented examination target during perimetry. The operation unit 37 is equipped with a mode switching switch, and a setting switch, and so on. The mode switching switch is used to switch a fundus photographing mode and a perimetry mode. The setting switch is employed to set a presentation position, luminance, a dimension, and the like of the examination target.

The image processing unit 32 performs an image processing operation such as a color tone correction with respect to images obtained by the camera 15 and the camera 18. The image switching unit 33 switches an observation image in the form of time-varying image obtained by the camera 15 and a photographed image in the form of a still image obtained by the camera 18 so that any one of the observation image and the photographed image is displayed on the monitor 31. The memory 34 stores therein the photographed image obtained by the camera 18 and response information (subjective information) obtained from the patient during perimetry. The memory 34 also stores therein a computer program by which a calculating process operation is carried out by employing a fuzzy theory. A method for objectively evaluating whether or not the patient has a disease by employing this fuzzy theory will now be explained in detail:

<Evaluation (Analysis) Method by Using Fuzzy Theory>

Formula 1 corresponds to a discriminating function using the fuzzy theory, and is used to compute whether or not a patient has a disease (namely, prevalence) by applying the response information obtained from the patient during perimetry to this formula 1.

Formula 1

$$z = a_1 x_1 + a_2 x_2 + a_3 x_3 + \cdots + a_n x_n \qquad \text{formula 1.}$$

In this formula 1, symbol "z" indicates an object variable, symbol "$x_n$" shows an explanatory variable, and symbol "$a_n$" represents a coefficient.

Figure 3:
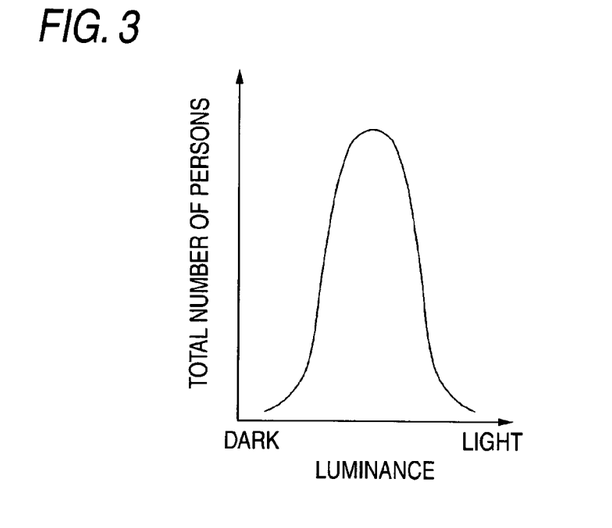
FIG. 3 is a diagram for representing a distribution of visual sensitivities with respect to luminance of stimulation light at respective examination points of a healthy person.

As the explanatory variable "$x_n$", such a value is employed which represents deviation. This deviation is obtained by comparing an actually measured value with a preliminarily collected normal value (healthy value) at each examination point on the fundus of the eye during perimetry. FIG. 3 is a graph indicative of a distribution of a visual sensitivity with respect to luminance of stimulation light at each examination point of a healthy person. In this graphic representation, an abscissa indicates luminance of stimulation light (stimulation target) which is presented to a patient, and an ordinates indicates a total number of persons who have visually recognized the stimulation light, i.e. a threshold value as to whether or not a visual sensitivity is present with respect to the luminance of the presented stimulation light. Therefore, this graphic representation corresponds to a deviation probability curve under the normal value. While the deviation probability curve as shown in FIG. 3 is employed, a value indicative of deviation of an actually measured value at each of the examination points is substituted for the explanatory variable "$x_n$." The deviation probability curve of this type may be preliminarily prepared depending on an age. Also, the deviation may be expressed by adjusting a reduction in an overall visual sensitivity which is caused by intermediate light transmission body opacity such as cataract or by a small pupil, and by adjusting high/low visual field hill which is caused by an abnormal high sensitivity.

Figure 4A:
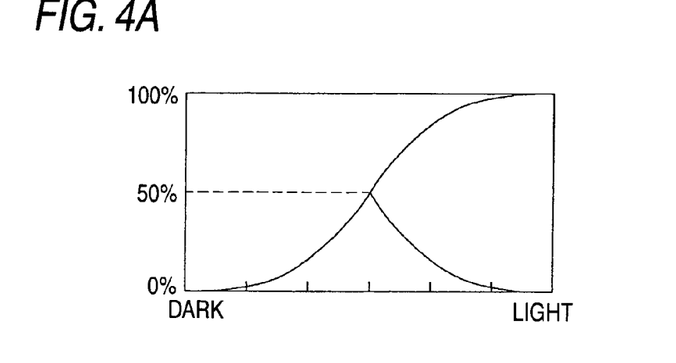
FIGS. 4A and 4B are diagrams for representing a membership function which is obtained based on a curve of probability-of-seeing.

The coefficient "$a_n$" corresponds to a value which is obtained from a probability function using a membership function. In this embodiment, this membership function is obtained from a curve of probability-of-seeing. As the membership function, such a curve (refer to FIG. 4(b)) is used which is obtained by bending a curve of probability-of-seeing shown in FIG. 4(a) at a position where the probability-of-seeing is equal to 50%. The probability-of-seeing curve shown in FIG. 4(a) represents probability-of-seeing with respect to luminance of stimulation light, and is obtained, by statistically collecting whether or not a healthy person can visually recognize stimulation light having certain luminance presented to the healthy person.

Figure 4B:
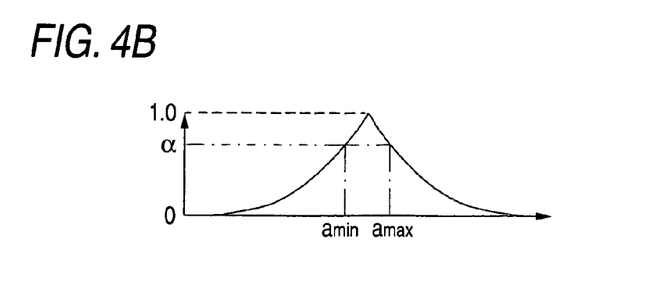

The membership function which is obtained based on the probability-of-seeing curve as shown in FIG. 4(b) is employed so as to obtain a range of prevalence in the case that the prevalence of a patient is obtained by applying the fuzzy theory. Assuming now that a maximum value of this membership function is equal to 1, a threshold value "$\alpha$ ($0<\alpha<1$)" is determined. The threshold value "$\alpha$" is employed so as to obtain both a maximum value and a minimum value of the coefficient "$a_n$." Both an object variable "z min" and another object variable "z max" are obtained by the coefficient "$a_n$" (both "a min" and "a max") determined by the threshold value "$\alpha$."

Figure 6:
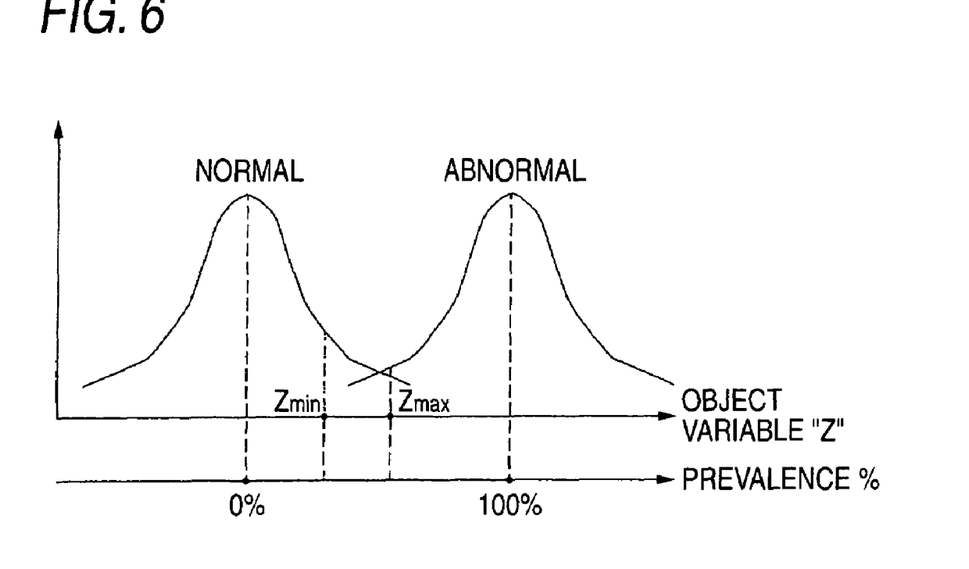
FIG. 6 is a diagram for showing a normal distribution obtained by an object variable.

Both the object variables "z min" and "z max" which have been obtained in this manner are applied to a graphic representation shown in FIG. 6 in order to calculate prevalence. FIG. 6 is a graphical representation of combined normal distributions which are obtained by respectively calculating an object variable "z" in a healthy person (normal) and an object variable "z" in a diseased person (abnormal), while applying the threshold value $\alpha=1$. In FIG. 6, it is so assumed that such an object variable "z" is prevalence of 0%, which corresponds to a maximum value of the normal distribution formed by the healthy person (average value of healthy person), whereas such an object variable "z" is prevalence of 100%, which corresponds to a maximum value of the normal distribution formed by the diseased person (average value of diseased person). By applying the obtained object variables "z min" and "z max" to the graphic representation of this type, the range of the prevalence can be obtained.

A description is made of operations as to the ophthalmic apparatus equipped with the above-described arrangement. Here, a perimetry method and a method for calculating prevalence based on actually measured values obtained at respective examination points are described.

Figure 7:
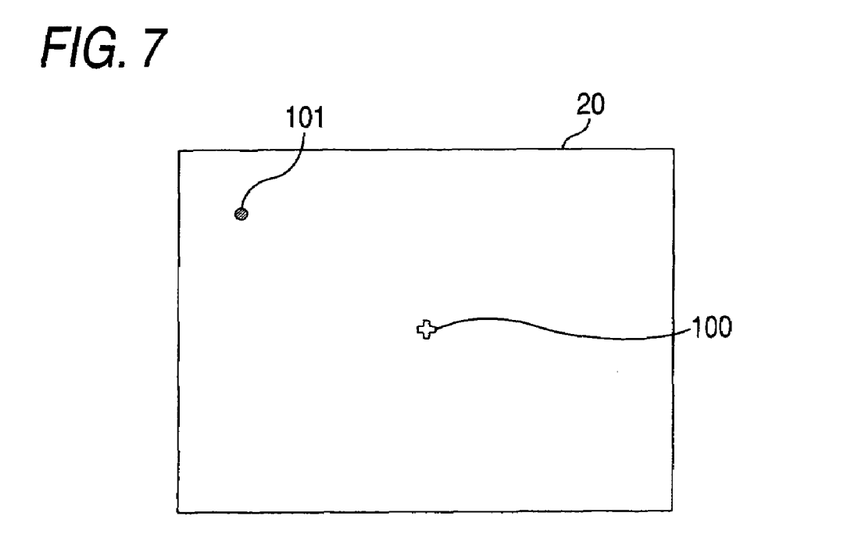
FIG. 7 is a diagram for showing a presentation example of examination targets by a liquid crystal display.

An examiner or doctor (hereafter referred to simply as the doctor) turns ON the light source 1 to illuminate the fundus Ef of the eye E with the infrared illumination light, and observes an image of the fundus Ef displayed on the monitor 31. Next, the doctor moves the lens 11 in the optical axis direction so that the image of the fundus Ef is clearly displayed on the monitor 31. After the image of the fundus Ef is clearly displayed on the monitor 31, the doctor sets the perimetry mode by manipulating the mode switching switch. The control unit 30 moves the mirror 17 out of the optical axis L2 when the perimetry mode is set. The control unit 30 displays an eye fixation target 100 at a center of the LCD 20 as illustrated in FIG. 7.

Next, the control unit 30 presents an examination target 101 at each of predetermined positions on the LCD 20, which correspond to the respective examination points on the fundus Ef, in accordance with the perimetry program preliminarily stored in the memory 34. For example, the examination targets 101 are sequentially presented around the eye fixation target 100 substantially coaxially or radially from an outer side with the eye fixation target 100 being located at a center. In this embodiment, 76 pieces of the examination targets 101 in total are sequentially presented substantially coaxially. Although the examination targets 101 are sequentially presented at the predetermined positions on the LCD 20 in accordance with the perimetry program in this embodiment, the present invention is not limited only to the above-descried example. For instance, the examination targets 101 may be presented at the respective preselected positions on the LCD 20 in the following manner. That is, for example, while a cursor (not shown) displayed on the monitor 31 is moved by manipulating the input device 36 so as to designate each of arbitrary positions of the fundus Ef, the examination targets 101 may be presented on the respective designated positions of the fundus Ef.

A patient maintains the eye fixation state, and if the patient can visually recognize the presented examination target 101, then the patient depresses the button 35 to notify the doctor and the ophthalmic apparatus of such a fact that the presented examination target 101 can be visually recognized. When the button 35 is depressed, the control unit 30 defines luminance of the presented examination target 101 at this time as a threshold value of a visually recognizable sensitivity of the patient at the examination point, and stores this threshold value of the visual sensitivity (simply referred to as "sensitivity" hereinafter) which corresponds to the luminance of the presented examination target 101 as response information (subjective information) into the memory 34.

In a case that the patient cannot visually recognize the presented examination target 101 (namely, button 35 is not depressed), the doctor operates a setting key of the operation unit 37 so as to increase luminance of the presented examination target 101 in a stepwise manner, thereby presenting the examination target 101 having different luminance on the LCD 20.

When the patient notifies that the presented examination target 101 can be visually recognized by depressing the button 35, the control unit 30, similarly to the aforementioned manner, defines luminance of the presented examination target 101 when the button 35 is depressed as a sensitivity of the patient at the examination point, and stores this sensitivity corresponding to the luminance of the presented examination target 101 as the response information into the memory 34. When the examination at the first examination point is accomplished, the control unit 30 changes the presentation position of the examination target 101 on the LCD 20, and presents the examination target 101 with respect to the next examination point. The examination points in the perimetry are set to be equal in condition to those which are employed to calculate the object variables "z" of the healthy person and the diseased person as shown in FIG. 6.

The sensitivities at the respective examination points are expressed in the unit of "dB (decibel)." Assuming now that luminance of a threshold value at a certain examination point is equal to "L" and maximum luminance of an examination target presented by the ophthalmic apparatus according to this embodiment is equal to "Lmax", a sensitivity Y(dB) at that examination point is expressed by the below-mentioned formula 2:

Formula 2

$$Y = 10 \times \log(Lmax/L) \qquad \text{formula 2}$$

For instance, if a sensitivity is obtained when the examination target is presented in the maximum luminance, then the sensitivity "Y" at that examination point becomes zero dB. Also, if a sensitivity is obtained when the examination target is presented in 1/100 of the maximum luminance, then the sensitivity "Y" at that examination point becomes 20 dB.

Figure 5A:
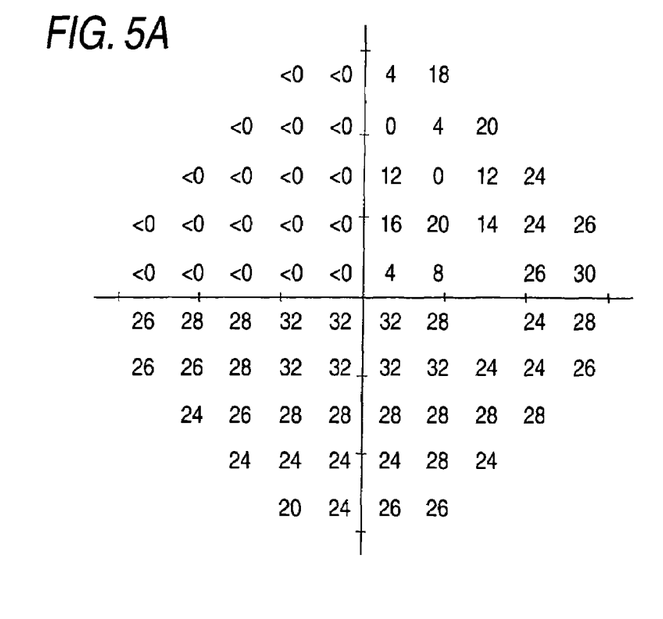
FIGS. 5A and 5B are diagrams for representing a distribution condition of sensitivities at all of the examination points of the fundus of eye.

When the sensitivities are obtained at all of the examination points, the control unit 30 displays a distribution condition of the sensitivities at all of the examination points on the monitor 31 by forming such a schematic diagram as shown in FIG. 5(a).

In FIG. 5(a), all of numeral values are expressed in the unit of "dB". Also, symbol (<0) shown in FIG. 5(a) represents that a sensitivity is lower than 0, namely indicates such a condition that although an examination target is presented in the maximum luminance, no sensitivity can be obtained. Further, a blank portion (corresponding to two points) shown in FIG. 5(a) is a portion corresponding to a blind spot.

When the doctor depresses (manipulates) the judgement button of the operation unit 37, the control unit 30 executes the perimetry program which has been stored in the memory 34 so as to calculate prevalence by employing the above-described formula 1. First, the control unit 30 obtains that the sensitivity obtained at each examination points is located in which set (probability) of the sensitivity distribution obtained from the deviation probability curve of FIG. 3. In this embodiment, 5 sets are prepared, namely, for example, a set smaller than 0.5% (<0.5) of the entire portion; another set equal to or larger than 0.5% and smaller than 1% (<1) of the entire portion; another set equal to or larger than 1% and smaller than 2% (<2) of the entire portion; another set equal to or larger than 2% and smaller than 5% (<5) of the entire portion; and also, another set equal to or larger than 5% (−) of the entire portion.

Figure 5B:
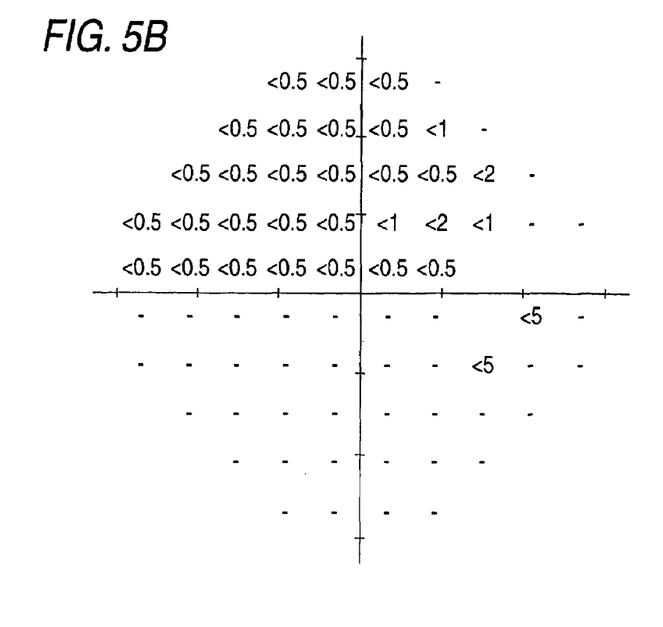

The control unit 30 classifies the sensitivity distribution (see FIG. 5(a)) of the patient, which has been obtained by executing the perimetry, into the aforementioned 5 sets every examination point (refer to FIG. 5(b)). The control unit 30 converts the classified value at each examination point into a numeral value indicative of deviation, and then, substitutes this numeral value for the above-explained formula 1 as the explanatory variable "$x_n$." That is, the values obtained at the respective examination points are substituted for all of $x_1, x_2, x_3, ---, x_n$ as the explanatory variables. Also, as to the coefficient "$a_n$" expressed in the formula 1, an upper limit (a max) and a lower limit (a min) of this coefficient "$a_n$" are determined by setting the threshold value "α (for instance, 0.8)" to the membership function given based upon the probability-of-seeing curve. The control unit 30 substitutes such values for the formula 1 to calculate the object variable "z". Furthermore, the control unit 30 applies the obtained object variables "z max" and "z min" to the above-explained normal distribution of FIG. 6 to calculate a range of the prevalence as an evaluation value. The obtained range of the prevalence is stored into the memory 34 along with the various sorts of data of the patient, and further, is displayed on the monitor 31. When a print switch of the operation unit 37 is depressed (manipulated), the range of the prevalence is printed out by a printer (not shown).

As explained above, since the prevalence is obtained by employing the fuzzy theory based on the examination result, the reference value that can be used in the evaluation is obtained. Therefore, even an less experienced examining person or doctor can quickly evaluate the examination result.

Although as the coefficient "$a_n$", only the minimum value and the maximum value thereof have been employed which have been obtained by setting the threshold values to the membership function in the above-described embodiment, the present invention is not limited thereto. Alternatively, for instance, the coefficient "$a_n$" may be changed at the respective examination points by applying different weights to the respective examination points by considering a sort of diseases such as retinitis pigmentosa and age-related macular degeneration, an age and an occupation of a patient, positions of respective examination points on the fundus of an eye, and the like. Also, the threshold value "α" which is applied to the membership function may be changed in various manners.

Although as the explanatory variables "$x_n$", the value indicative of the deviation of the actually measured values of the respective examination points by employing the deviation probability curve as shown in FIG. 3 has been employed in the above-described embodiment, the present invention is not limited. Alternatively, a response (whether or not sensitivity is obtained) of a patient may be processed in the form of a numeral value, and then, this numeral value may be substituted for the formula 1.

As described above, this embodiment has explained with reference to the ophthalmic apparatus equipped with the function of the fundus camera and the function of the perimeter. Alternatively, as apparent from the foregoing descriptions, the present invention may be applied to such a perimeter that examination targets are represented at respective points on the inside a semi-spherical perimetry dome. Furthermore, the present invention is not limited only to the perimeter, but may be applied to an ophthalmic apparatus, such as a subjective type refractive power measuring apparatus, for examining and evaluating a visual function of an eye of a patient based on a response from the patient.

What is claimed is:

1. An ophthalmic apparatus for examining and evaluating a visual function of an eye of a patient, comprising:
   a presentation unit which presents an examination target to the patient's eye;
   a storage unit which stores therein plural pieces of subjective information obtained from the patient as to whether or not the patient can visually recognize the presented examination target;
   a calculation unit which calculates an objective evaluation value for the patient's eye based upon the stored subjective information; and
   wherein the calculation unit performs multiple classification analysis using discriminating function expressed by a formula: $z = a_1 x_1 + a_2 x_2 + a_3 x_3 + \ldots + a_n x_n$ where z represents an object variable, $x_n$ represents an explanatory variable and $a_n$ represents a coefficient,
   wherein the plural pieces of stored subjective information are employed as the explanatory variable $x_n$,
   wherein values obtained by employing a membership function and a threshold α (0<α<1) are employed as a maximum value and a minimum value of the coefficient $a_n$, the membership function using a curve obtained by bending a curve of probability-of-seeing at a position where the probability-of-seeing is equal to 50%,
   wherein prevalence is obtained as an evaluation value by applying a minimum value z min and a maximum value z max of the object variables, obtained by the explanatory variable $x_n$ and the minimum value $a_{min}$ and the maximum value $a_{max}$ of the coefficient $a_n$, to a predetermined normal distribution representing prevalence, an output unit which outputs the calculated evaluation value.

2. An ophthalmic apparatus as claimed in claim 1, wherein:

the ophthalmic apparatus includes:
a perimeter for examining and evaluating a perimetric condition of the patient's eye.

3. An ophthalmic apparatus as claimed in claim 2, wherein:

the presentation unit presents, as the examination target, a perimetric stimulation target at each of various positions around a predetermined eye fixation point.

4. An ophthalmic apparatus for examining and evaluating a perimetric condition of an eye of a patient, comprising:

a presentation unit which presents an examination target at each of various positions around an eye fixation point to which the patient eye is visually fixed;

a storage unit which stores therein plural pieces of luminance information of the examination target when the patient can visually recognize the examination target presented at each position;

a calculation unit which calculates an objective evaluation value for the patient's eye based on the stored luminance information; and wherein the calculation unit performs multiple classification analysis using discriminating function expressed by a formula: $z = a_1 x_1 + a_2 x_2 + a_3 x_3 + \ldots + a_n x_n$ where z represents an object variable, $x_n$ represents an explanatory variable and $a_n$ represents a coefficient, wherein the plural pieces of stored luminance information are employed as the explanatory variable $x_n$, wherein values obtained by employing a membership function and a threshold $\alpha$ ($0 < \alpha < 1$) are employed as a maximum value and a minimum value of the coefficient $a_n$, the membership function using a curve obtained by bending a curve of probability-of-seeing at a position where the probability-of-seeing is equal to 50%, wherein prevalence is obtained as an evaluation value by applying a minimum value z min and a maximum value z max of the object variables, obtained by the explanatory variable $x_n$ and the minimum value $a_{min}$ and the maximum value $a_{max}$ of the coefficient $a_n$, to a predetermined normal distribution representing prevalence, an output unit which outputs the calculated evaluation value.

5. An ophthalmic apparatus as claimed in claim 4 wherein:

the storage unit stores therein a threshold value of a visual sensitivity corresponding to the luminance of the presented examination target as the luminance information when the patient can visually recognize the presented examination target.

* * * * *